United States Patent
Nwawka

Patent Number: 6,036,638
Date of Patent: Mar. 14, 2000

[54] VAGINAL SLEEVE

[76] Inventor: Chudi C. Nwawka, 8102 Chastain Dr., Atlanta, Ga. 30342

[21] Appl. No.: 08/963,995

[22] Filed: Nov. 4, 1997

[51] Int. Cl.⁷ .................................................. A61B 1/32
[52] U.S. Cl. ........................................... 600/186; 600/220
[58] Field of Search ................................. 128/830–841; 600/186, 203, 220

[56] References Cited

U.S. PATENT DOCUMENTS

| | | | |
|---|---|---|---|
| 3,841,317 | 10/1974 | Awais | 128/17 |
| 5,007,409 | 4/1991 | Pope | 128/17 |
| 5,113,873 | 5/1992 | Boarman | 128/830 |
| 5,209,241 | 5/1993 | Hardy | 128/842 |
| 5,243,966 | 9/1993 | Ng | 128/3 |
| 5,325,871 | 7/1994 | Reddy | 128/830 |
| 5,460,165 | 10/1995 | Mayes | 600/186 |
| 5,515,862 | 5/1996 | Artsi et al. | 128/830 |

Primary Examiner—Michael A. Brown
Attorney, Agent, or Firm—Deveau & Marquis

[57] ABSTRACT

A vaginal sleeve used to cover the conventional vaginal speculum, generally comprising an elastomeric sheath having a small orifice at the distal end thereof a flange adapted to cover the pubic region, wherein the vaginal sleeve improves the physician's visibility during gynecological examination and surgical procedures, removes the need for using other medical instruments, such as retractors, by shoring the walls of the vaginal, and labia, from collapse, protects the walls of the vagina, and labia, during gynecological examinations and surgical procedures involving lasers and/or electricity, and further protect the vaginal region from speculum pinching during extraction.

11 Claims, 3 Drawing Sheets

VAGINAL SLEEVE

BACKGROUND OF THE INVENTION

1. Field of the Invention

The present invention relates generally to a sleeve, or cover, for a vaginal speculum Preferably, the vaginal sleeve comprises a latex sheath having a small orifice at the distal end thereof. At the proximal end of the sleeve, a flange is adapted to cover the pubic region, the lower part of the abdomen, groin region, inner thighs, and perineum. The flange, among other things, protects and excludes vaginal hair from interfering with the examination process. The present invention improves the physician's visibility during gynecological examination and surgical procedures, removes the need for using other medical instruments, such as retractors, by shoring the walls of the vagina, and labia, from collapse, protects the walls of the vagina, and labia, during gynecological examinations and surgical procedures, and further protects the vaginal region from specula pinching during extraction. The flange and sheath protect the vulva and other covered areas from laser beams and electrical current when they are used in gynecological procedures.

2. Background of the Art

Vaginal specula are well known in the art of medical devices. For example, the bi-valve, duck-billed speculum is the most common device for gynecological examination used by medical professionals practicing in OB-GYN care. A speculum is primarily used to give the examining physician and surgeon an unobstructed view of the vaginal cavity. It is also used to keep the vaginal walls from collapsing during medical procedures, such as LEEP, laser, and cauterization, where damage to the vaginal walls is probable should they come in contact with the laser or electrode used during such gynecological procedures.

Devices for covering/sheathing the arms of a speculum are known to exist. These disclose devices are intended to protect patients and medical professionals from the spread of infectious disease. These sheaths are disposable. For example, U.S. Pat. No. 5,234,966 to Ng, discloses a method and apparatus for sheathing and protecting speculum arms. The Ng apparatus and method obviates the need for cleaning and sterilizing speculum arms after use in vaginal and/or uterine examinations. The sheaths covering the arms are disposable and protect the physician conducting the vaginal examination from contact with body discharges including the possibility of contaminated blood. U.S. Pat. No. 5,460,165 to Mayes discloses another such protective sheath for the speculum arms.

There further exist several known patents in the field of female condoms, for example, U.S. Pat. No. 5,515,862 to Artisi et al., U.S. Pat. No. 5,325,871 to Reddy U.S. Pat. No. 5,209,241 to Hardy and U.S. Pat. No. 5,113,873 to Boarman. Generally, these devices relate to barrier methods of contraception and protection from sexually transmitted diseases. In particular, they disclose types of female condoms, most having an extended shield protecting the area surrounding the genitalia. Further, they are devices that allow the female to control the use of contraception, but unlike the "pill," protect the female from sexually transmitted diseases (STDs). Before such devices were available, the responsibility to protect women from STDs was the men's, a responsibility too often ignored Female condoms are neither intended, nor designed to provide the advantages of the present invention.

While there exist several devices for protecting speculum arms during examination and protecting the vaginal cavity during intercourse, none appear to disclose a method or apparatus that can: improve the physician's visibility during gynecological examinations and surgical procedures; remove the need for secondary instruments during surgery, like retractors, by shoring the walls of the vagina, and labia, from collapse; protect the walls of the vagina, and labia, during examinations and surgical procedures; protect the patient from specula pinching during extraction; and, protect the patient from laser and electrical injuries in the areas covered.

Thus, it can be seen that there is a need for a vaginal sleeve that, when used during gynecological examinations and surgeries, will improve visibility for the medical professional and protect the vaginal cavity and surrounding region from possible injury. It is the provision of such a method and apparatus to which the present invention is primarily directed.

SUMMARY OF THE INVENTION

The speculum is a common medical instrument used in gynecological examinations and surgeries. Typically, the speculum comprises one or two duck-billed arms and a pivoting mechanism so that the medical professional may adjust the relative position of the arms about a fulcrum. During examination, the speculum arms are inserted into the vaginal cavity, rotated about 90°, and spread apart to afford the examining physician greater visual and instrumental access into the vaginal cavity. Disposable specula do exist, but these have proven in practice to be cost inefficient. Therefore, most gynecological examinations and procedures are carried out using a metal speculum which, among other things, must be sterilized after each use.

Typically during gynecological exams and surgical procedures, the speculum arms are inserted into the vaginal cavity at an orientation when the arms are in a plane parallel to the vertical plane of the labia for the ease and comfort of the patient. After insertion, the speculum is normally rotated 90° degrees, and the speculum arms are slowly spread apart by a thumb press. In this position, optimally, the physician has an unobscured view of the cervix The line of view of the physician generally is directed through an aperture and between the arms of the speculum. In this position, the physician may conduct the gynecological exam and/or gynecological surgery. Many disadvantages for the patient and physician exist when using the conventional speculum in the conventional way, without the apparatus and method of the present invention.

While using the prior art specula without sheathing during gynecological examination, the walls of the vagina, labia and pubic hair tend to collapse in between the arms of the specula, which obscure the line of view of the physician between the aperture and the arms of the speculum. Vaginal wall collapse is especially common in women over 40, pregnant or recently delivered women, obese women, or in women with a combination of these conditions. The labia and pubic hair may further interfere with the physician's line of view. During the extraction of the speculum, it is typical that pubic hair, the labia, or even the vaginal walls may be pinched, which can cause the patient great discomfort and injury. During gynecological surgery, should the vaginal walls collapse in between the speculum arms, they may incur injuries from the cutting devices used during gynecological procedures, such as a laser or electrode. Even if the vaginal side walls do not collapse, the walls, if unprotected, may still be injured by a laser or electric current.

Further, physicians typically must insert secondary medical equipment, such as retractors, through the line of view, between the speculum arms, to keep the vaginal walls from collapsing. These devices are often difficult and cumbersome to precisely control and operate, while at the same time the physician attempts to operate the speculum Typically, the devices further reduce the already limited aperture through which work is performed. Mistakes in controlling either instrument can cause injury to the vaginal cavity and delay surgery.

Briefly described, in its preferred form, the present invention generally comprises a disposable, protective sheath designed to generally fully envelope the conventional vaginal speculum, particularly a bi-valve speculum, as used during gynecological examinations and surgical procedures. The sleeve may come packaged as a rolled, tube-shaped sheath, not unlike the packaged, conventional male condom. The present invention may further comprise a circular flange combination made from latex, or like material, designed to accommodate a standard bi-valve vaginal speculum. Before use, the preferred embodiment is unfurled to expose the device comprising a flange at the proximal end, and extending therefrom, the sheath running the general length of the speculum arms. The sheath terminates in a tip comprising a small hole.

The sleeve may further be provided with reinforcement, anti-sliding elements, such as a series of radial nibs, designed to prevent the present invention from sliding lengthwise along the speculum arms during insertion, use and extraction of the speculum The ribs also serve to reinforce the sides of the sleeve against collapse. A small opening is located at the distal end, or tip, of the sheath. The entire device, including the tip orifice, yields and enlarges when the blades of the speculum are pivoted and opened. At the proximal end of the sheath is a circular shaped flange which serves to exclude vaginal hair from the physician's line of view during gynecological examination, prevents the speculum from pinching the vaginal walls, and pulling the pubic hair during the examination process and pull-out. The present invention further prevents the walls of the vagina from collapsing in between the opened arms of the speculum and into the void created by the arms, which can obscure the view of the physician, and could cause injury to the vaginal cavity during surgery.

Accordingly, it is an object of the present invention to provide a method and apparatus which can quickly and easily retract and insulate the vaginal cavity during gynecological surgeries, like LEEP and laser cauterization procedures, and protect the lateral vaginal walls during gynecological exams.

It is another object of the present invention to provide a method and apparatus to prevent the side walls of the vagina from collapsing into the barrel of the speculum during a gynecological exam and/or surgical procedure.

Still another object of the present invention is to provide a method and apparatus to improve a physician's visibility into the vaginal cavity when using a conventional speculum.

Yet another object of the present invention is to provide a method and apparatus that will shorten the time needed for vaginal procedures.

Another object of the present invention is to provide a method and apparatus that will ease the discomfort the patient may experience during gynecological procedures.

Still another object of the present invention to provide a product that is constructed of durable goods and which is easy to install and remove.

Yet another object of the present invention to provide a product that is functionally effective and cost-efficient.

Another object of the present invention is to provide a product in a wide assortment of colors, sizes and materials to accommodate various needs.

These and other objects, features, and advantages of the present invention will become more apparent upon reading the following specification in conjunction with the accompanying drawing figures.

DETAILED DESCRIPTION OF A PREFERRED EMBODIMENT

Figure 1:
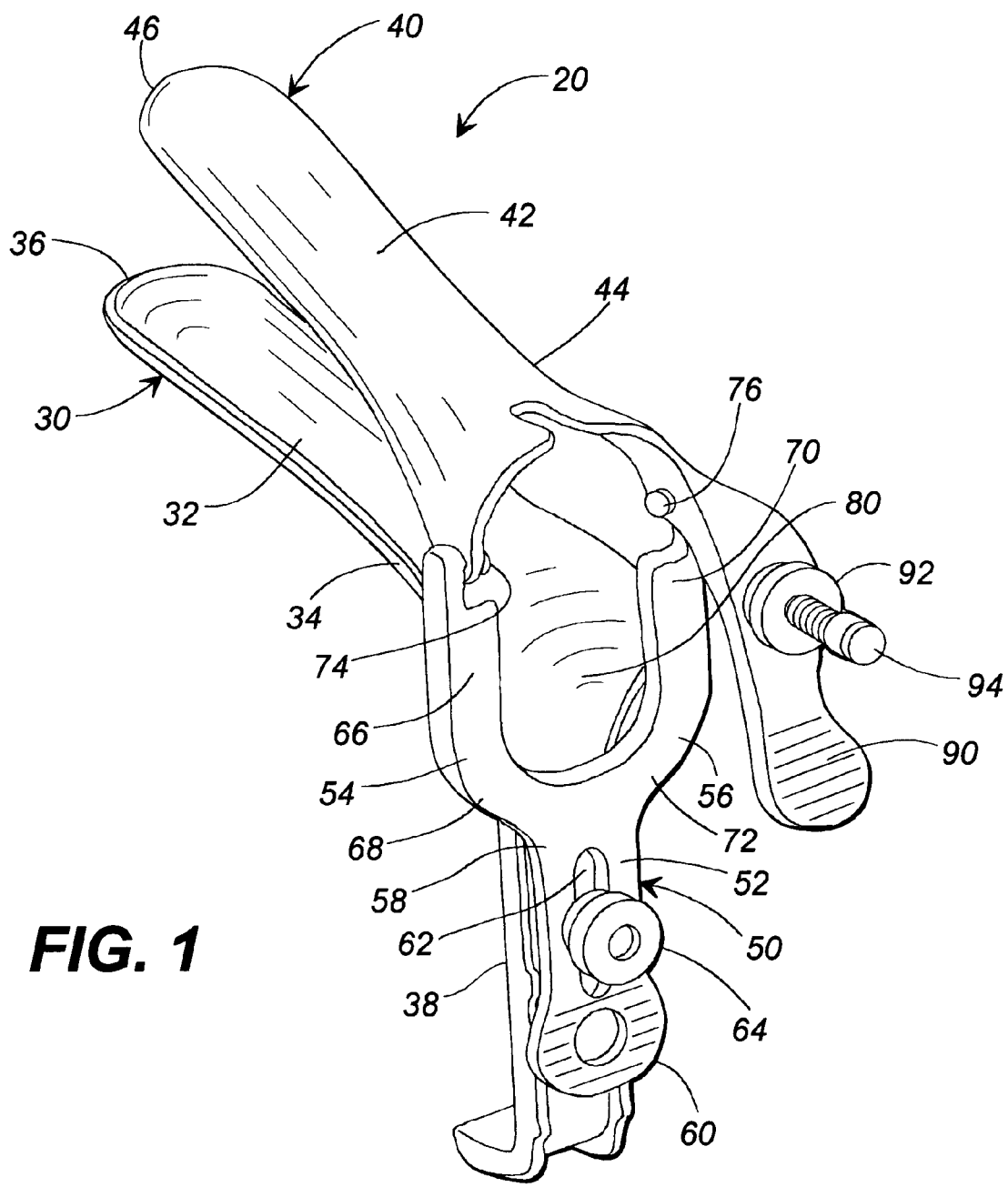
FIG. 1 is a perspective view of a conventional speculum used in gynecological exams.

Referring now in detail to the drawing figures, wherein like reference numerals represent like parts throughout the several views, FIG. 1 shows a conventional speculum 20, the type most commonly used in gynecological examinations. The speculum 20 comprises a lower arm 30, an upper arm 40, and a pivot mechanism 50.

The lower arm 30 comprises a blade 32 having a proximal end 34, a distal end 36, and a handle portion 38 which is integrally connected to the proximal end 34 of the blade 32. The upper arm 40 comprises a blade 42 having a proximal end 44 and a distal end 46. The arms 30, 40 of the speculum 20 are of substantially duck-billed shape for the ease of insertion of the arms 30, 40 into the vaginal cavity of a patient.

The pivot mechanism 50 is adjustably mounted to the handle portion 38 of the lower arm 30. The pivot mechanism 50 is substantially Y-shaped comprising a base member 52, a first fork 54 and a second fork 56.

The base member 52 of the pivot mechanism 50 has a upper end 58 and a lower end 60. The base member 52 has a slot 62 formed therethough extending lengthwise generally from upper end 58 to lower end 60. Further, slot 62 is located generally along the lengthwise line of bisection of base member 52. A first securing screw (not shown) fixed to the handle portion 38 of the lower arm 30 projects through the slot 62 thereby allowing the pivot mechanism 50 to be adjusted in relation to the lower arm 30. The adjustment extends to the limits defined by the slot 62. A securing nut 64 may be threadably secured to the first securing screw (not shown) to releasably secure the pivot mechanism 50 relative to the lower arm 30 at a fixed adjustment.

The first fork 54 of pivot mechanism 50 has a upper end 66 and a lower end 68. Likewise, the second fork 56 has a upper end 70 and a lower end 72. The upper ends 66, 70 of the first and second forks 54, 56 are integrally connected to the upper end 58 of the base member 52 and initially extends generally laterally from the base member 52 and thereafter curving to a position wherein the first and second forks 54, 56 extend substantially parallel to the base member 52.

A first pin 74 extends inwardly from the upper end 66 of the first fork 54 and a second pin 76 extends inwardly from the upper end 70 of the second fork 56. The proximal end 44 of the upper arm 40 is pivotally connected to the first and second pins 74, 76. The physician's line of view is through an examination aperture 80, which is formed between the forks 54, 56 of the pivot mechanism 50, the proximal end 34 of the blade 32 of the lower arm 30, and the proximal end 44 of blade 42 of the upper arm 40. The examination aperture 80 may be enlarged or reduced by adjusting the pivot mechanism 50 relative to the handle portion 38 of the lower arm 30.

A thumb press 90 connected to the proximal end 44 of the upper arm 40 is utilized by selectively moving the arms 30, 40 between an insertion position (not shown), wherein the lower and upper arms 30, 40 are positioned so that they lie generally in a plane parallel to the plane of the labia, and an examination position shown in FIG. 1, and described below. Therefore, upon insertion of arms 30, 40 into the vaginal cavity, the speculum 20 is turned approximately 90°, and into the examination position. If handle portion 38 is defined as resting in the 180° orientation in the examination position, as shown in FIG. 1, handle portion 38 would lie in either the 90° or 270° orientation in the insertion position.

In the inspection position, the proximal end 34 of the blade 32 of the lower arm 30 and the proximal end 44 of the blade 42 of the upper arm 40 are substantially adjacently disposed. In this position, the arms 30, 40 may be partially inserted into the vaginal cavity of the patient The speculum 20 is then turned from the insertion position to the examination position. The thumb press 90 is then pressed to move the upper arm 40 relatively to the lower arm 30, so that the upper and lower arms 30, 40 are disposed in an examination position wherein the proximal end 34 of the blade 32 of the lower arm 30 and the proximal end 44 of the blade 42 of the upper arm 40 are spaciously separated, as shown in FIG. 1. The maximum separation of the arms 30, 40 occurs between the distal ends 36, 46 of the arms 30, 40. As thumb press 90 is further pressed, upper arm 40 continues to rotate upwards about the pins 74, 76.

A second securing nut 92 may then be threadably secured to a second securing screw 94 which is connected to the pivot mechanism 50 and extends through an aperture (not shown) formed in the thumb press 90 to retain the arms 30, 40 in the examination position. The examining physician may then examine the patient by looking through the examination aperture 80 defined above.

Figure 2:
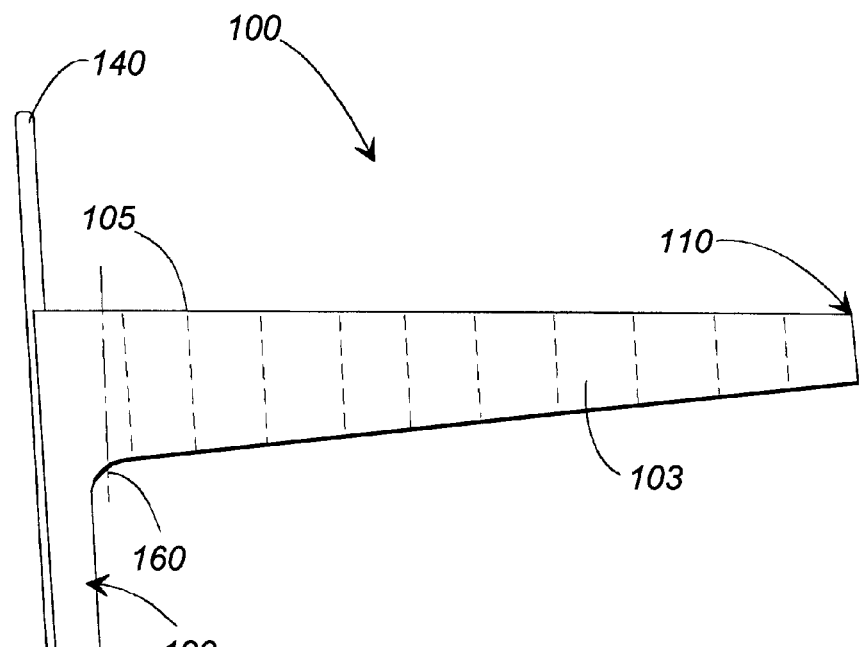
FIG. 2 is a side view of the present invention.
Figure 3:
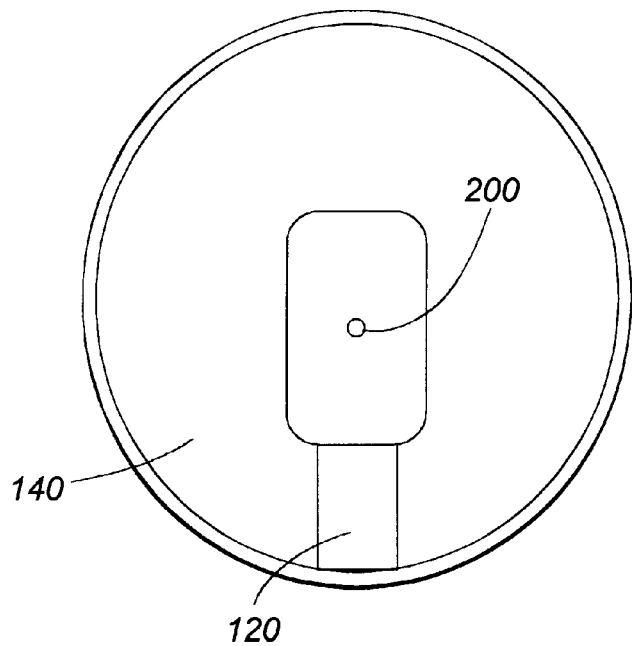
FIG. 3 is an end view of the present invention as shown FIG. 2.
Figure 4:
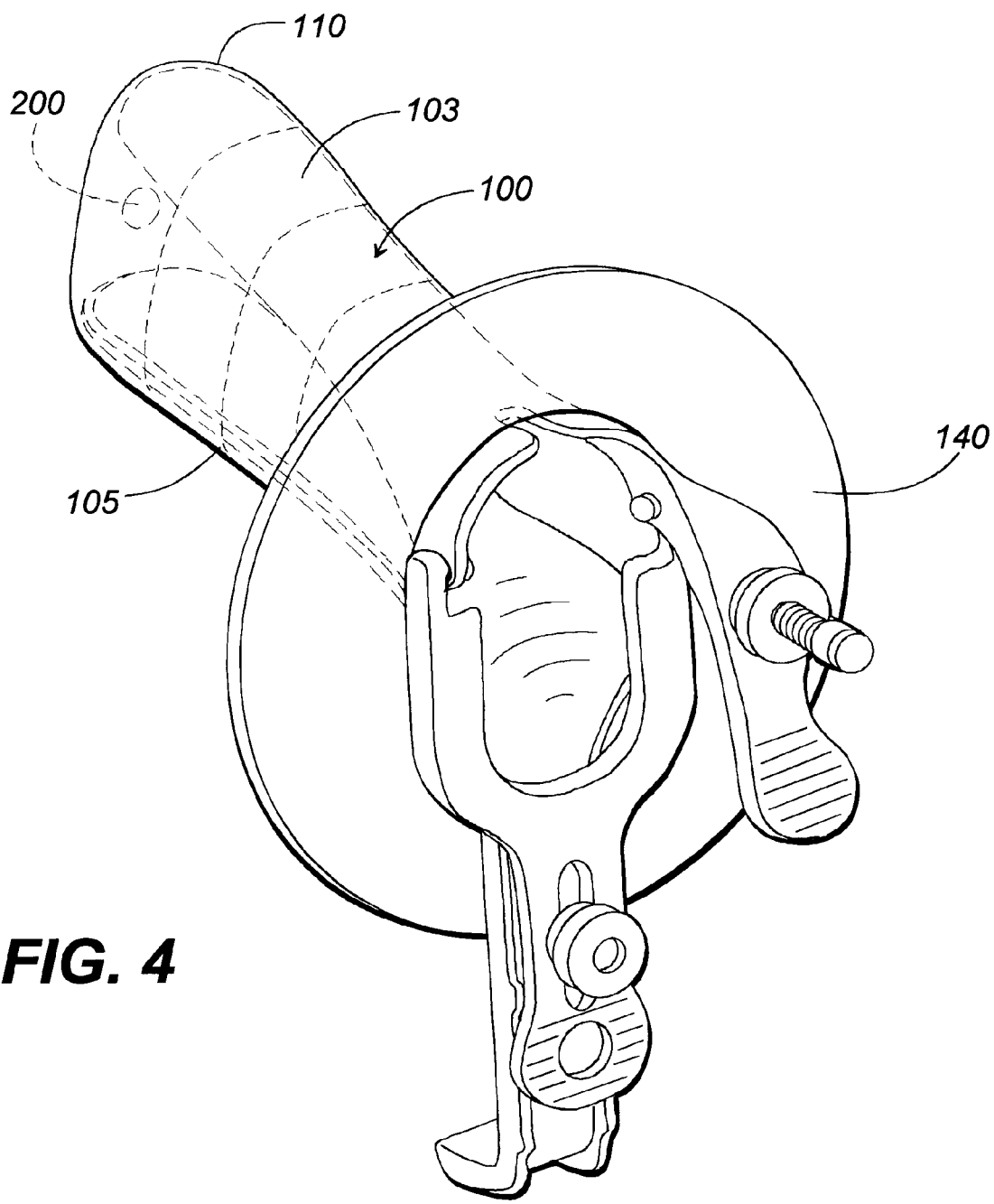
FIG. 4 is a perspective view of the present invention used in combination with the conventional speculum

Referring now to FIGS. 2–4, the vaginal sleeve 100, designed to envelope a conventional bi-valve vaginal speculum 20, comprises sheath 103 extending from proximal end 160 to the tip 110. The length of sheath 103 from proximal end 160 to the tip 110 is generally the length of the speculum arms 30, 40 of the speculum 20 used in the gynecological exam The size of the speculum 20 used during the examination varies between different doctors and patients; so, too, does the size of the vaginal sleeve 100 to accommodate different sized speculum Tip 110 of sheath 103 comprises a hole 200. Hole 200 is generally circular in shape and relatively small as compared to the area of tip 110. Preferably, hole 200 and tip 110 is comprised of reinforced material which would inhibit any deformation of hole 200 beyond that incurred by the general stretching of the sheath 103 by the speculum arms 30, 40 separated during examination.

Vaginal sleeve 100 may further comprise flange 140 located at the proximal end of the sheath 103, which is generally circular in shape and serves to exclude vaginal hair from the physician's line of view, and from coming in contact with speculum 20. Flange 140 may further comprise recess 120, adapted to fit handle portion 38 of the lower arm 30 of speculum 20. Recess 120 is generally rectangular in shape, in order to allow speculum 20 to be fully covered by vaginal sleeve 100 all the way to handle portion 38.

Sheath 103 may further comprise ribs 105 designed to prevent the sheath 103 from sliding while used with the speculum 20 during examination. Ribs 105 are spaced at regular intervals along the length of sheath 103. The ribs 105 also serve to reinforce the sides of the sleeve against collapse. It will be obvious to one skilled in the art that other anti-slip means may be used to retain sheath 103 on speculum 20 during examination and pull-out.

FIG. 4 shows one embodiment of the vaginal sleeve 100 used in combination with speculum 20. In this embodiment, flange 140 extends radially and covers only a portion of handle portion 38. Speculum arms 30, 40 are shown separated and opened.

Vaginal sleeve 100 comprises a material which will yield when the arms 30, 40 of speculum 20 are separated and opened. This material must not fail upon such expansion, but must have enough strength to shore the vaginal walls from collapse when arms 30, 40 are separated. Preferably, vaginal sleeve 100 comprises latex.

In preferred form, the gynecologist or obstetrician would slide the proximal end 160 of vaginal sleeve 100 over speculum arms 30, 40. The vaginal sleeve 100 is pulled to a point when flange 140 rests against the handle portion 38, as shown in FIG. 4. At this position, handle portion 38 securably rest in recess 120. Once the vaginal sleeve 100 is in place, the gynecologist inserts the sleeve 100 covering speculum 20 into the vaginal cavity of the patient as described above. During the examination, the gynecologist or obstetrician will separate the arms 30, 40 of speculum 20 by pressing down upon thumb press 90. Sheath 103, surrounding the arms 30, 40 will expand and prevent the vaginal walls, labia and hair from collapsing around the open arms 30, 40. As arms 30, 40 are separated, hole 200 at tip 110 will further expand. At this point, the physician's line of view should be unobscured through aperture 80, continue the length of arms 30, 40, and through hole 200, this entire length being sheathed and protected against any collapse of the vaginal walls. After use, the gynecologist or obstetrician removes the speculum 20 from the patient's vaginal cavity and discards the used sleeve 100.

While the invention has been disclosed in its preferred forms, it will be apparent to those skilled in the art that many modifications, additions, and deletions can be made therein without departing from the spirit and scope of the invention and its equivalents as set forth in the following claims.

What is claimed is:

1. An apparatus to cover a conventional vaginal speculum having a air of arms, comprising:

a sheath encircling and extending over the length of both of the arms of said conventional vaginal speculum the sheath having a distal end and a proximal end;

wherein the distal end of the sheath includes a tip;

said tip including a viewing orifice located to allow gynecological viewing through the orifice.

2. The apparatus of claim 1, wherein said sheath further comprises a generally circular shaped flange integrally attached to the proximal end of said sheath.

3. The apparatus of claim 2, wherein said sheath comprises a material which will yield when the said arms of said speculum are separated and opened, and will shore the vaginal walls from collapse when said arms of said speculum are separated.

4. The apparatus of claim 3, wherein said sheath further comprises anti-slip means which retains said sheath in place on said speculum arms during gynecological examinations and procedures.

5. The apparatus of claim 4, wherein said anti-slip means comprises ribs spaced at regular intervals along the length of said sheath.

6. The apparatus of claim 5, wherein said tip is comprised of reinforced material which inhibits deformation of the orifice beyond that incurred by the general stretching of said sheath by said speculum arms.

7. An apparatus to cover a conventional vaginal speculum having a pair of arms, comprising
- (a) a sheath encircling and extending over the length of both of the arms of said conventional vaginal speculum, the sheath having a distal end and a proximal end;
- (b) a generally circular shaped flange integrally attached to the proximal end of the sheath;
- (c) anti-slip means which retains the sheath in place on said speculum arms and serves to reinforce the sides of the sheath against collapse during use of said speculum;
- wherein the sheath comprises a material which will yield when the said arms of said speculum are separated and opened, and will shore the vaginal walls from collapse when said arms of said speculum are separated.

8. The apparatus of claim 7, wherein said anti-slip means includes nibs spaced at regular intervals along the length of said sheath.

9. The apparatus of claim 7, wherein the sheath further comprises a tip at the distal end of the sheath, the tip including a viewing orifice located to allow gynecological viewing through the orifice, and reinforcement material which inhibits deformation of the orifice beyond that incurred by general stretching of the sheath by said speculum arms.

10. A method to cover a conventional vaginal speculum having a pair of arms, which improves the examining professional's line of view during gynecological examinations and procedures, and reduces the risk of electrical, laser and mechanical injuries to the patient, comprising the steps of:
- (a) covering both of the arms of said conventional speculum with a material which will yield during use of said speculum, the material including a distal end and a proximal end, the distal end being provided with a viewing orifice located to allow gynecological viewing through the orifice;
- (b) inserting the arms of said speculum into the patient's vaginal cavity, and tuning said speculum into an examination position;
- (c) expanding the arms of said speculum during examination and/or surgery, and
- (d) viewing patient's vaginal cavity through an aperture in said speculum, and continuing through the orifice in the distal end of said covering material.

11. An apparatus to cover a conventional vaginal speculum having a handle and a pair of arms, comprising:
- (a) a sheath encircling and extending over the length of both of the arms of said conventional vaginal speculum, the sheath having a distal end and a proximal end; and
- (b) a flange integrally attached to the proximal end of the sheath, the flange including a recess designed to receive a portion of said handle of said speculum.

* * * * *